United States Patent
Tretjak et al.

(10) Patent No.: US 9,403,751 B2
(45) Date of Patent: Aug. 2, 2016

(54) LIQUID-LIQUID EXTRACTION PROCESS FOR THE PRODUCTION OF ACRYLIC ESTERS

(71) Applicant: Arkema France, Colombes (FR)

(72) Inventors: Serge Tretjak, Roulhing (FR); Stephane Denis, Leyviller (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 14/493,559

(22) Filed: Sep. 23, 2014

(65) Prior Publication Data
US 2015/0087857 A1    Mar. 26, 2015

(30) Foreign Application Priority Data
Sep. 23, 2013    (FR) ...................................... 13 59110

(51) Int. Cl.
| | | |
|---|---|---|
| C07C 67/58 | (2006.01) | |
| C07C 67/08 | (2006.01) | |
| B01J 4/00 | (2006.01) | |
| B01D 11/04 | (2006.01) | |

(52) U.S. Cl.
CPC ................ *C07C 67/58* (2013.01); *B01D 11/04* (2013.01); *B01D 11/043* (2013.01); *B01J 4/001* (2013.01); *C07C 67/08* (2013.01)

(58) Field of Classification Search
CPC ......... C07C 67/58; C07C 67/08; B01D 11/04
USPC ....................................................... 560/218
See application file for complete search history.

(56) References Cited

U.S. PATENT DOCUMENTS

| | | |
|---|---|---|
| 4,464,229 A | 8/1984 | Sato et al. |
| 5,435,892 A | 7/1995 | Mivazaki et al. |
| 2005/0189296 A1 | 9/2005 | Yada et al. |
| 2008/0183005 A1 | 7/2008 | Paul et al. |

FOREIGN PATENT DOCUMENTS

JP    EP 1721886 A1 * 11/2006    ......... B01D 11/0488

OTHER PUBLICATIONS

Perrry's Chemical Engineers Handbook; Robert H. Perry and Don W. Green; Liquid-Liquid Extraction Operations and Equipment—McGraw Hill, 1999 pp. 15-1, 15-32, 15-33, 15-2, 15-3.

\* cited by examiner

*Primary Examiner* — Yong Chu
(74) *Attorney, Agent, or Firm* — Lynn B. Morreale

(57) ABSTRACT

The invention relates to a liquid-liquid extraction process, comprising:
  the provision of a main input liquid stream, comprising at least one compound of interest and an excess compound;
  the provision of a liquid scrubbing stream;
  the extraction of the excess compound from the main input liquid stream by contact with the liquid scrubbing stream, making it possible to collect a main output liquid stream, depleted in excess compound with respect to the main input liquid stream;
in which:
  the main input liquid stream and the liquid scrubbing stream exhibit a difference in density of less than or equal to 50 kg/m$^3$ and also an interfacial tension of less than or equal to 3 dyn/cm; and
  the extraction stage is carried out in a packed contactor with a ratio by weight as input liquid scrubbing stream/main liquid stream ranging from 0.3 to 0.5.

The invention also relates to a process for the production of acrylic ester in which the production stream is treated by means of the above liquid-liquid extraction process.

8 Claims, 1 Drawing Sheet

LIQUID-LIQUID EXTRACTION PROCESS FOR THE PRODUCTION OF ACRYLIC ESTERS

CROSS-REFERENCE TO RELATED APPLICATIONS

This application claims benefit to French patent application FR 13.59110, filed Sep. 23, 2013.

FIELD OF THE INVENTION

The present invention relates to a liquid-liquid extraction process, and to the use of this process in the context of the production of acrylic esters, in particular methyl acrylate and ethyl acrylate.

TECHNICAL BACKGROUND

Processes are known for the manufacture of acrylic esters, in particular methyl acrylate and ethyl acrylate, by direct esterification of acrylic acid by the corresponding alcohol, for example catalysed by sulphuric acid. In such processes, large amounts of unreacted alcohol are collected at the outlet of the reactor.

For environmental and economic reasons, it is essential to recover the unreacted alcohol, in order generally to recycle it to the reactor.

To this end, it is known to distil the stream of products or also to scrub it using an aqueous stream.

The documents FR 2 509 294, U.S. Pat. No. 5,435,892 and FR 2 884 514 provide examples of such processes for the production of acrylic esters.

In the document EP 1 721 886, the crude acrylic ester mixture is subjected to different treatments targeted at separating the catalyst and at concentrating and purifying the desired product. These treatments can be carried out by scrubbing, neutralization and/or extraction. The equipment examples cited are mixers/decanters, extraction columns or stirred tanks. The extraction columns are of packed, plate or rotating disk type. The process for the production of methyl acrylate is illustrated using a treatment combining an extraction of the reaction mixture in a packed column with a filtration. However, the residual alcohol content of the extracted organic phase remains of the order of 0.1% to 0.2% by weight.

There still exists a need to succeed in more efficiently recovering the alcohol at the outlet of the reactor.

SUMMARY OF THE INVENTION

The invention relates first to a liquid-liquid extraction process, comprising:
- the provision of a main input liquid stream, comprising at least one compound of interest and an excess compound;
- the provision of a liquid scrubbing stream;
- the extraction of the excess compound from the main input liquid stream by contact with the liquid scrubbing stream, making it possible to collect a main output liquid stream, depleted in excess compound with respect to the main input liquid stream;

in which:
- the main input liquid stream and the liquid scrubbing stream exhibit a difference in density of less than or equal to 50 kg/m³ and also an interfacial tension of less than or equal to 3 dyn/cm; and
- the extraction stage is carried out in a packed contactor with a ratio by weight as input liquid scrubbing stream/main liquid stream ranging from 0.3 to 0.5.

According to one embodiment:
- the main input liquid stream is an organic stream and the liquid scrubbing stream is an aqueous stream;
- preferably, the compound of interest is an acrylic ester, more particularly preferably methyl acrylate and/or ethyl acrylate, and the excess compound is an alcohol, preferably methanol and/or ethanol.

According to one embodiment, the main input liquid stream comprises from 0.5% to 30% of excess compound, preferably from 1% to 20% and more particularly from 2% to 10%, and/or the main output liquid stream comprises less than 2000 ppm of excess compound, preferably less than 1000 ppm and more particularly less than 750 ppm, indeed even less than 500 ppm, According to one embodiment, the packed contactor comprises packing components exhibiting a diameter of greater than or equal to the critical diameter, expressed in m, resulting from the relationship $d_c = 2.42 \times (S \ast gc/\Delta\rho \ast g)^{0.5}$, S representing the interfacial tension between the main input liquid stream and the liquid scrubbing stream, expressed in N/m, $\Delta\rho$ representing the difference in density between the main input liquid stream and the liquid scrubbing stream, expressed in kg/m³, gc being the conversion factor for the gravitational constant (kg·m/N·s²) and g being the gravitational constant (9.83 m/s²).

According to one embodiment, the specific surface of the packing (random or stacked) of the contactor is greater than or equal to 200 m²/m³.

Another subject-matter of the invention is a process for the production of acrylic ester comprising:
- the feeding of a reactor with acrylic acid, with catalyst and with alcohol;
- the withdrawal of an acrylic ester stream at the outlet of the reactor;
- the liquid-liquid extraction of the acrylic ester stream by an aqueous stream, which makes it possible to collect a purified acrylic ester stream, the liquid-liquid extraction being carried out according to the process described above, in which the main input liquid stream is the acrylic ester stream, the liquid scrubbing stream is the aqueous stream, the main output liquid stream is the purified acrylic ester stream, the compound of interest is the acrylic ester and the excess compound is the alcohol.

According to one embodiment, the purified acrylic ester stream is additionally subjected to one or more distillation stages in order to remove additional organic compounds.

According to one embodiment, the process comprises a settling stage at the outlet of the reactor, making it possible to collect an aqueous phase in addition to the acrylic ester stream, the aqueous phase being distilled in order to recover, on the one hand, a fraction rich in alcohol which is recycled to the reactor and, on the other hand, a fraction rich in water which is used as liquid scrubbing stream in the liquid-liquid extraction stage.

According to one embodiment, the process comprises the collecting of an aqueous stream enriched in alcohol on conclusion of the liquid-liquid extraction stage and the combining of this with the aqueous phase resulting from the reactor.

Another subject-matter of the invention is a plant for the production of acrylic ester, comprising:
- a reactor fed via a pipe for introducing acrylic acid, a pipe for introducing alcohol and a pipe for introducing catalyst;
- a pipe for collecting acrylic ester at the outlet of the reactor;

a liquid-liquid extraction unit, comprising a packed contactor, fed via the pipe for collecting acrylic ester and also via a pipe for feeding with liquid scrubbing stream;
a pipe for collecting purified acrylic ester at the outlet of the liquid-liquid extraction unit.

According to the invention, the extraction unit comprises a packed contactor comprising packing components exhibiting a diameter of greater than or equal to the critical diameter, expressed in m, resulting from the relationship $d_c = 2.42 \times (S*gc/\Delta\rho*g)^{0.5}$, S representing the interfacial tension between the acrylic ester stream and the liquid scrubbing stream, expressed in N/m, $\Delta\rho$ representing the difference in density between the main input liquid stream and the liquid scrubbing stream, expressed in kg/m$^3$, gc being the conversion factor for the gravitational constant (kg·m/N·s$^2$) and g being the gravitational constant (9.83 m/s$^2$).

According to one embodiment, the pipe for collecting purified acrylic ester feeds one or more distillation units.

According to one embodiment, the plant comprises:
a pipe for collecting aqueous phase at the outlet of the reactor;
an aqueous/alcoholic distillation unit, fed via the pipe for collecting aqueous phase and optionally in addition via a pipe for collecting aqueous stream enriched in alcohol resulting from the liquid-liquid extraction unit, the pipe for feeding with liquid scrubbing stream being connected at the outlet of the aqueous/alcoholic distillation unit;
a pipe for collecting fraction rich in alcohol, connected at the outlet of the aqueous/alcoholic distillation unit and feeding the reactor.

According to one embodiment, the pipe for introducing alcohol is a pipe for introducing methanol or a pipe for introducing ethanol.

The present invention makes it possible to overcome the disadvantages of the state of the art. It more particularly provides a means for recovery of the unreacted alcohol at the outlet of a reactor for the production of acrylic ester which is more efficient.

This is accomplished by virtue of an improved liquid-liquid extraction, based on the use of a packed contactor.

This is because the inventors have discovered that, when the liquid streams in contact in a liquid-liquid extraction unit exhibit a small difference in density and a low interfacial tension, the use of such a packed contactor is more advantageous than that of a conventional mechanically stirred contactor, in that it offers a greater productivity (at a similar extraction performance), it being specified that other types of contactors, such as centrifugal contactors, for example, exhibit the disadvantage of being more complex and thus more expensive.

Liquid streams having the abovementioned properties present a specific difficulty in treatment as the separation has a tendency to be not very efficient, as a result of a relatively high droplet size (greater than 0.6 mm). A tendency towards blocking has in particular been observed in mechanically stirred contactors, unless used at low throughputs.

Thus, the invention makes it possible to use a contactor which is smaller in size and less expensive in order to achieve the desired productivity and the desired specifications for residual alcohol content in the stream of products.

DESCRIPTION OF EMBODIMENTS OF THE INVENTION

The invention is now described in more detail and without implied limitation in the description which follows.

The percentages shown are percentages by weight, unless otherwise mentioned.

Production of Acrylic Ester

For the sake of simplicity of the account, the liquid-liquid extraction process of the invention is described with reference to a process for the production of acrylic ester.

Figure 1:
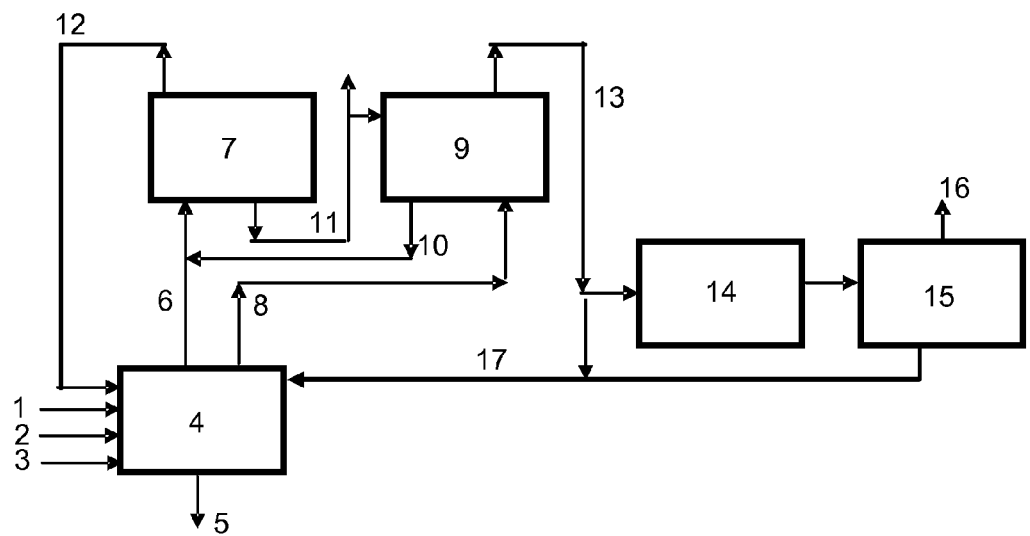
FIG. 1 diagrammatically represents a plant for the production of acrylic ester according to one embodiment of the invention.

With reference to FIG. 1, a plant for the production of acrylic ester according to the invention comprises a reactor 4. The reactor 4 is fed via a pipe for introducing acrylic acid 2, a pipe for introducing alcohol 3 and a pipe for introducing catalyst 1.

According to one embodiment, the alcohol is methanol. According to another embodiment, the alcohol is ethanol. A mixture of methanol and ethanol is also possible. Use may be made, as catalyst, for example, of sulphuric acid or an organic sulphonic acid, such as methanesulphonic acid, para-toluenesulphonic acid, benzenesulphonic acid, dodecylsulphonic acid or their mixtures.

At the outlet of the reactor 4, the heavy products are removed via a collection of bleed of heavy products 5.

By means of a decanter (not represented) associated with the reactor 4, the following are recovered at the outlet of the reactor 4: on the one hand, an acrylic ester stream via a pipe for collecting acrylic ester 8, and, on the other hand, an aqueous phase (also comprising a portion of the unreacted alcohol) via a pipe for collecting aqueous phase 6.

The acrylic ester stream comprises acrylic ester as "compound of interest" (within the meaning of the invention), and also byproducts, contaminants and unreacted reactants and in particular the abovementioned alcohol compound, which constitutes the "excess compound" within the meaning of the invention.

The acrylic ester (compound of interest) is preferably methyl acrylate and/or ethyl acrylate. The unreacted alcohol (excess compound) is preferably methanol and/or ethanol.

The acrylic ester stream can comprise, for example, from 50% to 98% of acrylic ester, preferably from 70% to 97% and more particularly from 80% to 95%. The same acrylic ester stream can comprise, for example, from 0.5% to 30% of unreacted alcohol, preferably from 1% to 20% and more particularly from 2% to 10%.

The acrylic ester stream described above constitutes the "main input liquid stream" within the meaning of the invention.

The pipe for collecting aqueous phase 6 feeds an aqueous/alcoholic distillation unit 7. This aqueous/alcoholic distillation unit 7 makes it possible to recover the unreacted alcohol and to recycle it to the reactor 4 via a pipe for collecting the fraction rich in alcohol 12. The remainder of the aqueous phase (fraction rich in water) is recovered at the bottom of the aqueous/alcoholic distillation unit 7 in order to be used as liquid scrubbing stream (within the meaning of the invention), via a line known as pipe for feeding with liquid scrubbing stream 11. It should be noted that not all of this stream is necessarily used as liquid scrubbing stream, it being possible for a portion to be removed, as is represented in the diagram by the vertical arrow.

The pipe for feeding with liquid scrubbing stream 11 and the pipe for collecting acrylic ester 8 both feed a liquid-liquid extraction unit 9, in which a liquid-liquid extraction is carried out between the two streams, making it possible to transfer the excess compound (unreacted alcohol) from the acrylic ester stream to the liquid scrubbing stream.

The liquid-liquid extraction unit is operated with a ratio by weight as input liquid scrubbing stream/main liquid stream ranging from 0.3 to 0.5. This is because it has been shown that, below a ratio by weight of 0.3, the excess compound still remained present at a high content in the main output liquid stream. In particular, for a ratio by weight of 0.3 in a process for the production of acrylic ester, the residual alcohol in the purified output acrylic ester stream is greater than 3000 ppm, which is not compatible with the final uses of this monomer. Furthermore, the use of a ratio greater than 0.5 implies the use of a large volume of scrubbing liquid and the use of a larger extraction column in order to obtain the same extraction effectiveness, which is not economically advantageous.

This liquid-liquid extraction unit 9 is described in more detail below.

At the outlet of the liquid-liquid extraction unit 9 are connected, on the one hand, a pipe for collecting purified acrylic ester 13 (in order to recover the acrylic ester stream depleted in alcohol) and, on the other hand, a pipe for collecting the aqueous stream enriched in alcohol 10 (in order to recover the liquid scrubbing stream enriched in alcohol).

The pipe for collecting the aqueous stream enriched in alcohol 10 returns to the aqueous/alcoholic distillation unit 7: the (scrubbing) stream enriched in alcohol is thus combined with the aqueous phase resulting from the reactor, making it possible to recover and to recycle the alcohol present in it.

The pipe for collecting purified acrylic ester 13 feeds successive distillation units 14, 15, which make it possible to remove other undesirable compounds and to recover the acrylic ester in its final form via a line for collecting final product 16. One or more recycling lines 17 can be provided in order to return a portion of the stream to the reactor 4, which are fed by the pipe for collecting purified acrylic ester 13 and/or the successive distillation units 14, 15.

The residual alcohol content of the stream covered in the pipe for purified acrylic ester 13 is preferably less than or equal to 2000 ppm or 1000 ppm, for example less than or equal to 750 or 500 ppm.

Liquid-Liquid Extraction Unit

The invention provides for the use of a packed contactor for the above liquid-liquid extraction unit 9. According to one embodiment, the liquid-liquid extraction unit 9 consists of a single packed contactor or of a plurality of packed contactors positioned in series or in parallel. According to an alternative embodiment, the liquid-liquid extraction unit 9 additionally comprises a contactor of another type, for example a mechanically stirred contactor. According to yet another embodiment, additional means for removing the excess compound are associated with the liquid-liquid extraction unit (for example, a distillation unit).

The term "packed contactor" is understood to mean an appliance comprising a chamber in which two liquids are brought into contact, the chamber comprising a packing. The term "packing" is understood to mean a solid structure capable of increasing the contact surface area between the two liquids.

Preferably, the packed contactor is a static contactor, that is to say devoid of mechanical stirring means (such as paddles, turbines and the like) in the abovementioned chamber.

Figure 2:
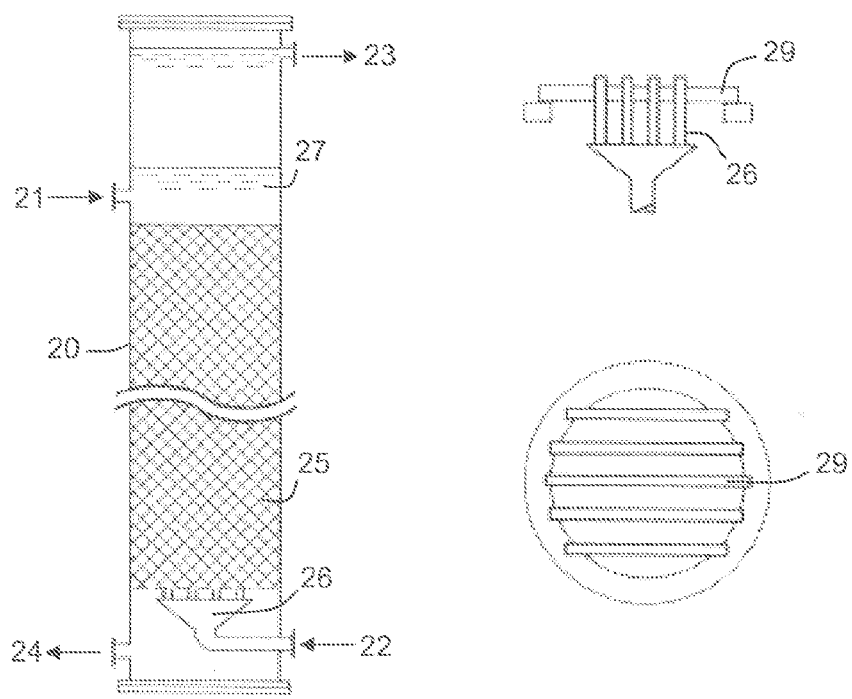
FIG. 2 illustrates an example of a packed contactor which can be used in the context of the invention. The left-hand drawing is a cross sectional view of the contactor along a vertical plane. The right-hand drawings are views of details of the appliance (cross section along a vertical plane at the top and along a horizontal plane at the bottom).

With reference to FIG. 2, an example of a packed contactor which can be used in the context of the invention comprises a column 20 forming a chamber. A pipe for feeding with heavy phase 21 and a pipe for feeding with light phase 22 are connected as inputs of the column 20, respectively at the top and at the bottom of the latter. A pipe for collecting light phase 23 and a pipe for collecting heavy phase 24 are connected at the outlet of the column 20, respectively at the top and at the bottom of the latter.

The column 20 comprises a packing 25 which rests on a plate 29 in the form of a grid. A distribution system 26 is provided at the level of the entry of the pipe for feeding with light phase 22. This distribution system 26 comprises, for example, an assembly of nozzles, in order to make it possible to generate drops of light phase in the heavy phase. It is positioned below the plate 29 and can pass through the latter.

A settling region 27 is inserted above the packing 25, which region makes possible the separation of the heavy phase and of the light phase. The throughputs are adjusted so that the interface between the phases is located between the pipe for feeding with heavy phase 21 and the pipe for collecting light phase 23 (placed above the preceding pipe).

In the context of the production of acrylic esters described above, the light phase is the main liquid stream (acrylic ester stream) and the heavy phase is the liquid scrubbing stream (of aqueous nature).

The heavy phase is the continuous phase, in which are dispersed drops of light phase in the packing 25.

The extraction temperature is preferably from 20 to 50° C. The ratio by weight as input heavy phase I light phase is preferably from 0.3 to 0.5.

The packing can be a random packing or a stacked packing or optionally a combination of the two, preferably a random packing. A random packing is composed of piled porous objects, the packing components, which can, for example, have an essentially cylindrical external shape. A stacked packing is composed of a single porous three dimensional structure or of a structure in the form of blocks arranged one above the other and/or one beside the other.

The packing can be manufactured with a ceramic or metal or glass, indeed even optionally plastic, material. The preferred material is stainless steel.

The external diameter of the packing components (in the case of a random packing) is preferably from 5 to 50 mm. Generally, this external diameter is chosen to be greater than or equal to the critical diameter $d_c$ presented in Perry's Chemical Engineer's Handbook, 7th edition, authors R. H. Perry and D. W. Green, chapter 15—Liquid-liquid extraction operations and equipment). The diameter $d_c$, expressed in m, results from the relationship $d_c = 2.42 \times (S*gc/\Delta\rho*g)^{0.5}$, S representing the interfacial tension between the main input liquid stream and the liquid scrubbing stream, expressed in N/m, $\Delta\rho$ representing the difference in density between the main input liquid stream (acrylic ester stream) and the liquid scrubbing stream, expressed in kg/m$^3$, gc being the conversion factor for the gravitational constant (kg·m/N·s$^2$) and g being the gravitational constant (9.83 m/s$^2$).

Under these conditions, the size of the drops formed and consequently the exchange area are virtually independent of the choice of the packing.

Preferably, the diameter of the packing components is less than one tenth of the diameter of the extraction column, in order to reduce the fouling of the column.

The packing components can, for example, be Raschig rings, Pall rings, saddle rings, Berl saddles or Intalox saddles. Alternatively, beads might also be used. Preferably, the specific surface of the packing components is greater than or equal to 200 m$^2$/m$^3$.

When a stacked packing is used, it is advantageously chosen so that it exhibits a surface area/volume ratio of at least 200 m$^2$/m$^3$, for example of at least 250 m$^2$/m$^3$, or of at least 500 m$^2$/m$^3$. Possible stacked packings available commercially are the BX packing from Sulzer, at 250 m$^2$/m$^3$, and Mellapack 750Y, also from Sulzer, at 750 m$^2$/m$^3$.

EXAMPLE

The following example illustrates the invention without limiting it.

In this example, the efficiency of a packed contactor and of a mechanically stirred contactor in carrying out the liquid-liquid extraction of the methanol present in a methyl acrylate stream is compared.

Use is made, as mechanically stirred contactor, of a column of Kuhni 150/30 G type having a height of 3.9 m, with five sections of 420 mm each comprising six stirrers. The diameter of the column is 150 mm and the column comprises a settling region at the top and a straightening region at the bottom.

Use is made, as packed contactor, of a column with a diameter of 180 mm and with an active height of 4 to 5 m. The packing consists of Pall rings with a diameter of 16 mm and with a specific surface of 205 m$^2$/m$^3$. The decanter at the top exhibits a diameter of 150 mm and a straightening region is provided at the bottom.

The stream to be treated (organic stream) is withdrawn from a plant for the production of methyl acrylate. It comprises 91.09% of methyl acrylate and 5.03% of methanol. The other main compounds detected in the stream are methyl acetate (1.94%) and acrylic acid (0.21%).

The scrubbing stream is an aqueous phase comprising 0.1% of methanol.

The difference in density between the column top product and the product at the bottom is, in this case, 30 kg/m$^3$. The densities of the products are measured at 20° C. using a volumetric flask and confirmed with ASPEN simulation software. The interfacial tension is 3 dyn/cm. It is measured at 20° C. by virtue of an IT Concept drop tensiometer, equipped with a computer, with a syringe driver of Exmire type, with a camera and with a glass vessel, the assembly being combined with a Haake thermostatically controlled bath.

The results obtained with the mechanically stirred contactor, under different operational conditions, are collated in Table 1 below. In this table, OP denotes the organic phase and AP denotes the aqueous phase.

TABLE 1

Results obtained with the mechanically stirred contactor

| OP throughput as input (kg/h) | AP throughput as input (kg/h) | OP throughput as output (kg/h) | AP throughput as output (kg/h) | AP/OP ratio at the inlet | Productivity (m$^3$/m$^2$/h) | Residual methanol content in OP as output (ppm) | Stirring speed (rpm) |
|---|---|---|---|---|---|---|---|
| 144.7 | 58.1 | 136.0 | 70.8 | 0.401 | 11.9 | 139 | 130 |
| 144.7 | 58.1 | 136.0 | 70.8 | 0.401 | 11.9 | 139 | 110 |
| 178.0 | 74.2 | 161.0 | 93.5 | 0.417 | 14.8 | 134 | 90 |
| 176.5 | 74.6 | 133.1 | 96.0 | 0.423 | 14.8 | 128 | 100 |
| 166.1 | 62.9 | 143.2 | 75.3 | 0.379 | 13.5 | 129 | 100 |
| 134.6 | 62.0 | 110.0 | 86.3 | 0.460 | 11.5 | 114 | 110 |
| 171.0 | 76.8 | 136.0 | 114.2 | 0.449 | 14.6 | 118 | 100 |
| 196.9 | 83.5 | 183.0 | 100.5 | 0.424 | 16.5 | 138 | 90 |
| 123.3 | 52.0 | 107.3 | 65.7 | 0.422 | 10.3 | 159 | 90 |
| 127.1 | 52.0 | 123.3 | 58.4 | 0.409 | 10.5 | 144 | 90 |
| 218.4 | 87.7 | | | 0.401 | 18.0 | B | 75 |
| 204.0 | 102.0 | | | 0.500 | 18.0 | B | 100 |

It is found that the mechanically stirred contactor makes it possible to obtain a desired residual methanol content (generally less than 1000 ppm). On the other hand, the system exhibits a tendency to become blocked (letter B in the table) when the specific throughput borders on 18 m$^3$/m$^2$/h. The blocking corresponds to an organic phase which stagnates, preventing any movement in the column and thus any separation.

The results obtained with the packed contactor, under different operational conditions, are collated in Table 2 below.

TABLE 2

Results obtained with the packed contactor

| OP throughput as input (kg/h) | AP throughput as input (kg/h) | OP throughput as output (kg/h) | AP throughput as output (kg/h) | AP/OP ratio at the inlet | Productivity (m$^3$/m$^2$/h) | Residual methanol content in OP as output (ppm) |
|---|---|---|---|---|---|---|
| 474 | 166 | 400 | 235 | 0.350 | 26.2 | 1134 |
| 565.6 | 185.2 | 473 | 293 | 0.327 | 30.7 | 360 |
| 513 | 179 | 437 | 271 | 0.349 | 28.3 | 604 |
| 328 | 163 | 280 | 195 | 0.497 | 20.0 | 604 |
| 350.4 | 125 | 290 | 183.4 | 0.357 | 19.4 | 1117 |
| 489 | 182.0 | 412 | 266 | 0.372 | 27.4 | 277 |

TABLE 2-continued

Results obtained with the packed contactor

| OP through-put as input (kg/h) | AP through-put as input (kg/h) | OP through-put as output (kg/h) | AP through-put as output (kg/h) | AP/OP ratio at the inlet | Productivity ($m^3/m^2/h$) | Residual methanol content in OP as output (ppm) |
|---|---|---|---|---|---|---|
| 499 | 180.6 | 420 | 270.6 | 0.362 | 27.8 | 824 |
| 499 | 200.4 | 420 | 272.4 | 0.402 | 28.6 | 239 |
| 492 | 147.0 | 418 | 225 | 0.299 | 26.2 | 1091 |
| 239.5 | 83.7 | 204 | 126.6 | 0.349 | 13.2 | 3538 |
| 635 | 220.0 | 522 | 324.4 | 0.346 | 35.0 | 519 |

It is found that the packed contactor also offers suitable separation performances while allowing a specific throughput from 1.5 to 2 times greater than that achievable with the mechanically stirred column.

This advantageous result, obtained with a static contactor, can also be achieved in other liquid-liquid extraction configurations, when the difference in density and the interfacial tension between the two liquid streams are low.

The invention claimed is:

1. A liquid liquid extraction process, comprising the steps of:
providing a main input liquid stream, comprising at least acrylic ester and an excess compound which is an alcohol;
providing a liquid scrubbing stream which is an aqueous stream;
extracting alcohol from the main input liquid stream by contact with the liquid scrubbing stream, thereby collecting a main output liquid stream, depleted in alcohol with respect to the main input liquid stream;
wherein:
the main input liquid stream and the liquid scrubbing stream exhibit a difference in density of less than or equal to 50 kg/m$^3$ and an interfacial tension of less than or equal to 3 dyn/cm; and
the extraction stage is carried out in a packed contactor having packing components with a specific surface greater than or equal to 200 m$^2$/m$^3$ and with a ratio by weight as input liquid scrubbing stream/main liquid stream ranging from 0.3 to 0.5.

2. The process according to claim 1, in which:
the excess compound is an alcohol selected from the group consisting of methanol ethanol, and mixtures thereof.

3. The process according to claim 1, in which the main input liquid stream comprises from 0.5% to 30% of excess compound, and/or in which the main output liquid stream comprises less than 2000 ppm of excess compound.

4. The process according to claim 1, in which the packed contactor comprises packing components exhibiting a diameter of greater than or equal to the critical diameter, expressed in m, resulting from the relationship $d_c=2.42\times(S^*gc/\Delta\rho^*g)^{0.5}$, S representing the interfacial tension between the main input liquid stream and the liquid scrubbing stream, expressed in N/m, $\Delta\rho$ representing the difference in density between the main input liquid stream and the liquid scrubbing stream, expressed in kg/m$^3$, gc being the conversion factor for the gravitational constant (kg.m/N.s$^2$) and g being the gravitational constant (9.83 m/s$^2$).

5. A process for the production of acrylic ester comprising the steps of:
feeding a reactor with acrylic acid, catalyst and alcohol;
withdrawing an acrylic ester stream at an outlet of the reactor;
liquid-liquid extraction of the acrylic ester stream by an aqueous stream, thereby collecting a purified acrylic ester stream, the liquid-liquid extraction being carried out according to the process of claim 1, wherein the main input liquid stream is the acrylic ester stream, the liquid scrubbing stream is the aqueous stream, the main output liquid stream is the purified acrylic ester stream, the compound of interest is the acrylic ester and the excess compound is the alcohol.

6. The process according to claim 5, in which the purified acrylic ester stream is additionally subjected to one or more distillation stages in order to remove additional organic compounds.

7. The process according to claim 5 wherein the outlet of the reactor comprises a settling stage to collect an aqueous phase in addition to the acrylic ester stream, the aqueous phase being distilled to recover, on the one hand, a fraction rich in alcohol which is recycled to the reactor and, on the other hand, a fraction rich in water which is used as liquid scrubbing stream in the liquid-liquid extraction stage.

8. The process according to claim 7, comprising the step of collecting an aqueous stream enriched in alcohol at the end of the liquid-liquid extraction stage and combining this with the aqueous phase resulting from the reactor.

* * * * *